United States Patent
Duke et al.

(10) Patent No.: US 8,843,321 B2
(45) Date of Patent: Sep. 23, 2014

(54) METHODS AND SYSTEMS FOR PROCESSING GLUCOSE DATA MEASURED FROM A PERSON HAVING DIABETES

(75) Inventors: David L. Duke, Fishers, IN (US); Abhishek S. Soni, Indianapolis, IN (US); Stefan Weinert, Pendleton, IN (US)

(73) Assignee: Roche Diagnostics Operations, Inc., Indianapolis, IN (US)

(*) Notice: Subject to any disclaimer, the term of this patent is extended or adjusted under 35 U.S.C. 154(b) by 1219 days.

(21) Appl. No.: 12/693,701

(22) Filed: Jan. 26, 2010

(65) Prior Publication Data

US 2011/0184267 A1    Jul. 28, 2011

(51) Int. Cl.
| G01N 33/48 | (2006.01) |
| G01N 31/00 | (2006.01) |
| G06G 7/48 | (2006.01) |
| G06G 7/58 | (2006.01) |
| A61B 5/145 | (2006.01) |
| A61B 5/00 | (2006.01) |

(52) U.S. Cl.
CPC ........... *A61B 5/14532* (2013.01); *A61B 5/7221* (2013.01); *A61B 5/725* (2013.01)
USPC ............ 702/19; 702/22; 703/11; 703/12

(58) Field of Classification Search
None
See application file for complete search history.

(56) References Cited

U.S. PATENT DOCUMENTS

| 6,882,940 B2 | 4/2005 | Potts et al. |
| 6,923,763 B1 | 8/2005 | Kovatchev et al. |
| 7,188,034 B2 | 3/2007 | Staib et al. |
| 7,389,133 B1 | 6/2008 | Kotulla et al. |
| 7,647,237 B2 * | 1/2010 | Malave et al. ............... 705/3 |
| 2004/0133079 A1 | 7/2004 | Mazar et al. |

FOREIGN PATENT DOCUMENTS

| JP | 04-134916 | 5/1992 |
| WO | WO0224065 A1 | 3/2002 |
| WO | WO2009047569 A2 | 4/2009 |

OTHER PUBLICATIONS

Parker, Robert S., et al, A Model-Based Algorithm for Blood Glucose Control in Type I Diabetic Patients, IEEE Transactions of Biomedical Engineering, vol. 46, No. 2, Feb. 1999.
Rapoport, et al., Optimal Filtering in the Presence of Faulty Measurement Biases, Proceedings of the 41st IEEE Conference on Decision and Control, Dec. 2002, pp. 2236-2241, Las Vegas, NV, USA.

* cited by examiner

*Primary Examiner* — Larry D Riggs, II
(74) *Attorney, Agent, or Firm* — Roche Diagnostics Operations, Inc.

(57) ABSTRACT

Methods and systems are disclosed for estimating a glucose level of a person having diabetes comprises. One method may comprise: receiving into a computing device a plurality of measured glucose results from a glucose sensor coupled to the person; using the computing device to analyze the plurality of measured glucose results with a probability analysis tool configured to determine a probability of glucose sensor accuracy based on the plurality of measured glucose results; and using the computing device to estimate a glucose level of the person with a recursive filter configured to estimate the glucose level based on the plurality of measured glucose results weighted with the probability of glucose sensor accuracy.

58 Claims, 8 Drawing Sheets

US 8,843,321 B2

METHODS AND SYSTEMS FOR PROCESSING GLUCOSE DATA MEASURED FROM A PERSON HAVING DIABETES

TECHNICAL FIELD

The present invention generally relates to processing glucose data measured from a person having diabetes and, in particular, for estimating the actual glucose level of the person in the presence of glucose sensor noise and/or glucose sensor malfunction.

BACKGROUND

As background, people suffer from either Type I or Type II diabetes in which the sugar level in the blood is not properly regulated by the body. Many of these people may use a continuous glucose monitoring (CGM) to monitor their glucose level on an ongoing basis. In order to perform CGM, a glucose sensor may be placed under the skin which is capable of measuring the glucose level of the person in the interstitial fluid. The glucose sensor may periodically measure the glucose level of the person at a known time interval, such as every one minute, and transmit the results of the glucose measurement result to an insulin pump, blood glucose meter, smart phone or other electronic monitor.

In some cases, the measured glucose results (from the glucose sensor) may contain sensor "noise" which causes them to deviate from the actual glucose level of the person. Sensor noise may be due to, for example, physical movement of the glucose sensor relative to the skin or due to electrical noise which may be inherent in the sensor itself. Furthermore, the glucose sensor may malfunction from time to time, such that the measured glucose results (from the glucose sensor) may be substantially different than the actual glucose level of the person. The glucose sensor may malfunction in this manner due to, for example, failure of the sensor electronics or battery or due to sensor "dropout." Sensor dropout may occur due to physiological problems with the glucose sensor's attachment to the person, such as movement of the sensor relative to the person. Sensor dropout may cause the measured glucose results "drop" to near zero, although the actual glucose level of the person may be much higher.

As a result, embodiments of the present disclosure may process the measured glucose results from the person such that the actual glucose level of the person may be estimated, even in the presence of sensor noise and/or sensor malfunction. In addition, the future glucose level of the person may be predicted, based on the estimated glucose level.

SUMMARY

In one embodiment, a method for estimating a glucose level of a person having diabetes comprises: receiving into a computing device a plurality of measured glucose results from a glucose sensor coupled to the person; using the computing device to analyze the plurality of measured glucose results with a probability analysis tool configured to determine a probability of glucose sensor accuracy $P_A$ based on the plurality of measured glucose results; and using the computing device to estimate a glucose level of the person with a recursive filter configured to estimate the glucose level based on the plurality of measured glucose results weighted with the probability of glucose sensor accuracy $P_A$.

In another embodiment, a computer-readable medium is disclosed having computer-executable instructions for performing a method for estimating a glucose level of a person having diabetes, wherein the method comprises: receiving into a computer a plurality of measured glucose results from a glucose sensor coupled to the person; using the computer to analyze the plurality of measured glucose results with a probability analysis tool configured to determine a probability of glucose sensor accuracy $P_A$ based on the plurality of measured glucose results; and using the computer to estimate a glucose level of the person with a recursive filter configured to estimate the glucose level based on the plurality of measured glucose results weighted with the probability of glucose sensor accuracy $P_A$.

In still another embodiment, an apparatus for estimating a glucose level of a person having diabetes comprises a microcontroller, an input device, and a display, wherein: the microcontroller is electrically coupled to the input device configured to receive a plurality of measured glucose results from a glucose sensor coupled to the person, wherein the microcontroller is configured to receive the plurality of measured glucose results from the input device; the microcontroller is configured to analyze the plurality of measured glucose results with a probability analysis tool configured to determine a probability of glucose sensor accuracy $P_A$ based on the plurality of measured glucose results; the microcontroller is configured to estimate a glucose level of the person with a recursive filter configured to estimate the glucose level based on the plurality of measured glucose results weighted with the probability of glucose sensor accuracy $P_A$; and the microcontroller is electrically coupled to the display such that the microcontroller is configured to transmit to the display information related to the estimate of the glucose level of the person.

BRIEF DESCRIPTION OF THE DRAWINGS

The embodiments set forth in the drawings are illustrative and exemplary in nature and not intended to limit the inventions defined by the claims. The following detailed description of the illustrative embodiments can be understood when read in conjunction with the following drawings, where like structure is indicated with like reference numerals and in which:

DETAILED DESCRIPTION

The embodiments described herein generally relate to methods and systems for processing glucose data measured from a person having diabetes and, in particular, for estimating the actual glucose level of the person in the presence of sensor noise and/or sensor malfunction. For the purposes of defining the present disclosure, the "measured glucose results" are the glucose levels of the person as measured by the glucose sensor; the "actual glucose level" is the actual glucose level of the person; and the "estimated glucose level" is the estimated glucose level of the person, which may be based on the measured glucose results.

Figure 1:
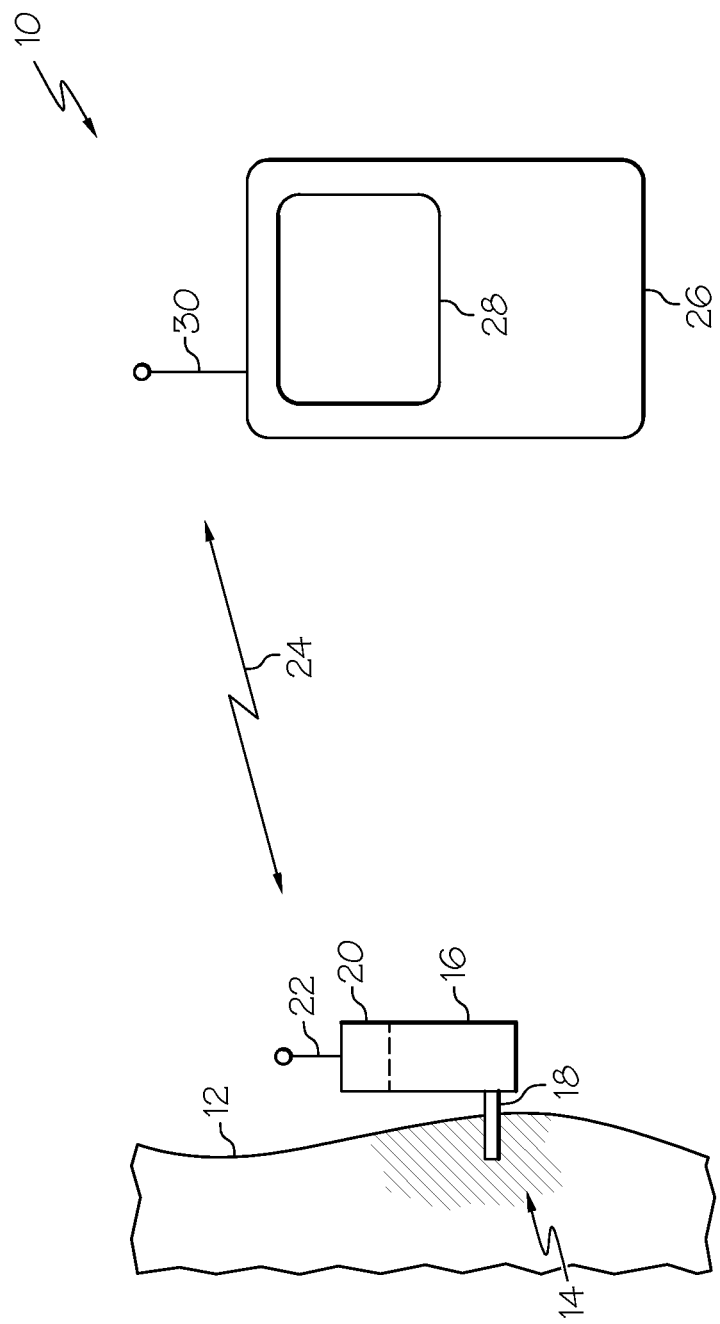
FIG. 1 depicts a continuous glucose monitoring (CGM) system according to one or more embodiments shown and described herein.

FIG. 1 depicts a continuous glucose monitoring (CGM) system 10 which may be used to continuously measure the glucose level of the person. The CGM system 10 may comprise a glucose sensor 16 having a needle 18 which may be inserted under the skin 12 of the person having diabetes. The end of the needle 18 may be located in interstitial fluid 14, such that measurements taken by the glucose sensor 16 are based on the level of glucose in the interstitial fluid 14. The glucose sensor 16 may be placed on the abdomen of the person or other suitable location and may be secured with tape or adhesive (not shown). Furthermore, the glucose sensor 16 may be periodically calibrated in order to improve its accuracy. This periodic calibration may help correct for sensor drift due to sensor degradation and changes in the physiological condition of the sensor insertion site. The glucose sensor 16 may comprise other components as well, including but not limited to a wireless transmitter 20 and an antenna 22. Although depicted in FIG. 1 as a having a rectangular shape, it is contemplated that the glucose sensor 16 may assume other geometric shapes as well. Although the glucose sensor 16 may use a needle 18 to gain access to the person's blood, it may also use other suitable devices to access the person's blood or other fluid in order to take glucose measurements, including those yet to be discovered.

The glucose sensor 16, upon taking a measurement, may transmit the measured glucose result via a communication link 24 to a glucose monitor 26. The communication link 24 may be wireless, such as radio frequency, or "RF," in which the measured glucose results are transmitted via electromagnetic waves. For example, "Bluetooth®" is one type of wireless RF communication system which uses a frequency of approximately 2.4 Gigahertz (GHz). Another type of wireless communication scheme may use infrared light, such as the systems supported by the Infrared Data Association® (IrDA®). Other types of wireless communication are also contemplated, including present technologies and yet-to-be-developed technologies. The communication link 24 may be unidirectional (i.e., data may be transmitted only from the glucose sensor 16 to the glucose monitor 26), or it may be bidirectional (i.e., data may be transmitted between the glucose sensor 16 and the glucose monitor 26 in either direction). Furthermore, the communication link 24 may permit communication between two or more devices (e.g., a glucose sensor, a glucose monitor, an insulin pump, and so forth). Although FIG. 1 shows the communication link 24 as being wireless, it may alternatively be a wired link, such as for example Ethernet. Other public or proprietary wired or wireless links may be used as well.

Figure 2:
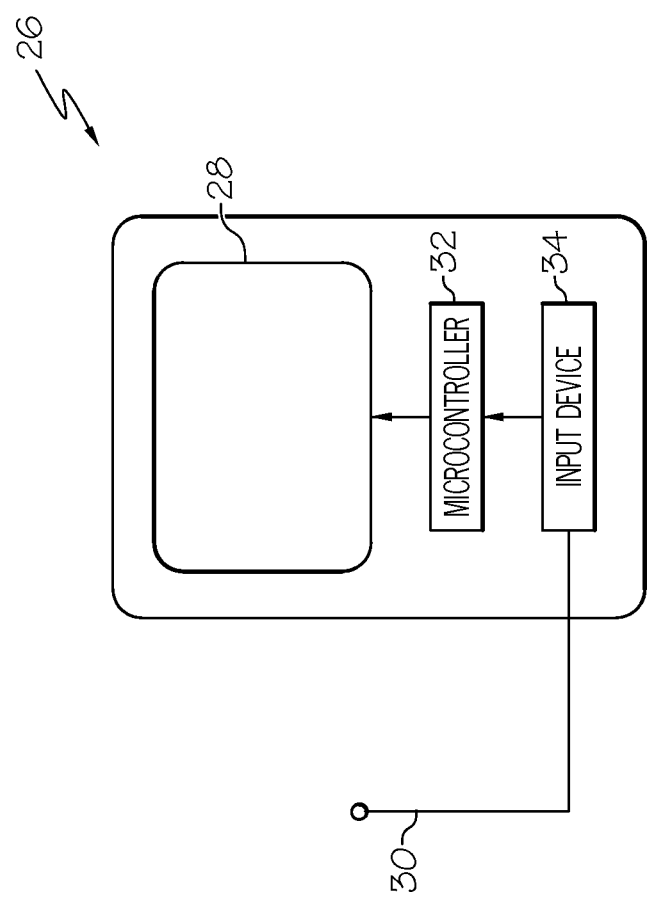
FIG. 2 depicts a glucose monitor according to one or more embodiments shown and described herein.

FIG. 2 illustrates one embodiment of a glucose monitor 26, which may comprise a display 28, a microcontroller 32, and an input device 34. Examples of the glucose monitor 26 include but are not limited to a blood glucose meter, an insulin pump, a cellular phone, a smart phone, a personal digital assistant, a personal computer, or a computer server. The microcontroller 32 may be electrically coupled to the input device 34, which may be configured to receive a plurality of measured glucose results from a glucose sensor coupled to the person. The microcontroller 32 may be configured to receive the plurality of measured glucose results from the input device 34. The glucose monitor 26 may also be configured to store in memory (not shown) a plurality of measured glucose results received from the glucose sensor 16 over a period of time. The microcontroller 32 may be further configured to analyze the plurality of measured glucose results with a probability analysis tool configured to determine a probability of malfunction for the glucose sensor. Furthermore, the microcontroller 32 may be configured to estimate a glucose level of the person using a recursive filter configured to weight the plurality of measured glucose results with the probability of glucose sensor accuracy. Finally, the microcontroller 32 may be electrically coupled to the display 28 such that the microcontroller is configured to transmit to the display 28 information related to the estimated glucose level of the person. As discussed herein, the displayed information may include the estimated glucose level of the person and/or a predicted glucose level of the person at some time in the future. Furthermore, the display may also include an estimate of the quality or uncertainty of the estimated glucose level. Moreover, the displayed information may include warnings, alerts, etc. regarding whether the estimated or predicted glucose levels of the person is hypoglycemic or will become hypoglycemic at some time in the future. This may take place, for example, if the person's glucose level falls below (or is predicted to fall below) a predetermined hypoglycemic threshold, such as 50 milligrams of glucose per deciliter of blood (mg/dl).

The microcontroller 32 may be an 8-bit device, a 16-bit device, or any other suitable device, and may have on-chip peripherals which facilitate its operation. For example, the microcontroller 32 may have internal memory for storing a computer program, internal memory for data storage, and internal memory for non-volatile storage of parameters used by the microcontroller during its operation. Furthermore, the microcontroller 32 may have timers, serial communication ports, interrupt controllers, and so forth. The microcontroller 32 may also be part of an application-specific integrated circuit (ASIC) that may include other circuitry which facilitates the operation of the glucose monitor 26. The input device 34 may be a wireless communication module configured to wirelessly receive measured glucose results from a glucose sensor (as shown in FIG. 1). As such, an antenna 30 may be used to improve the robustness of the wireless connection. Alternatively, the input device 34 may be a wired communication module that receives the measured glucose results through a wired connection, such as for example via Ethernet or similar protocol. The display 28 may comprise a liquid crystal display (LCD) or other suitable technology. The display 28 may also be configured to tactilely communicate information to the person, such as for example by vibrating.

Figure 3:
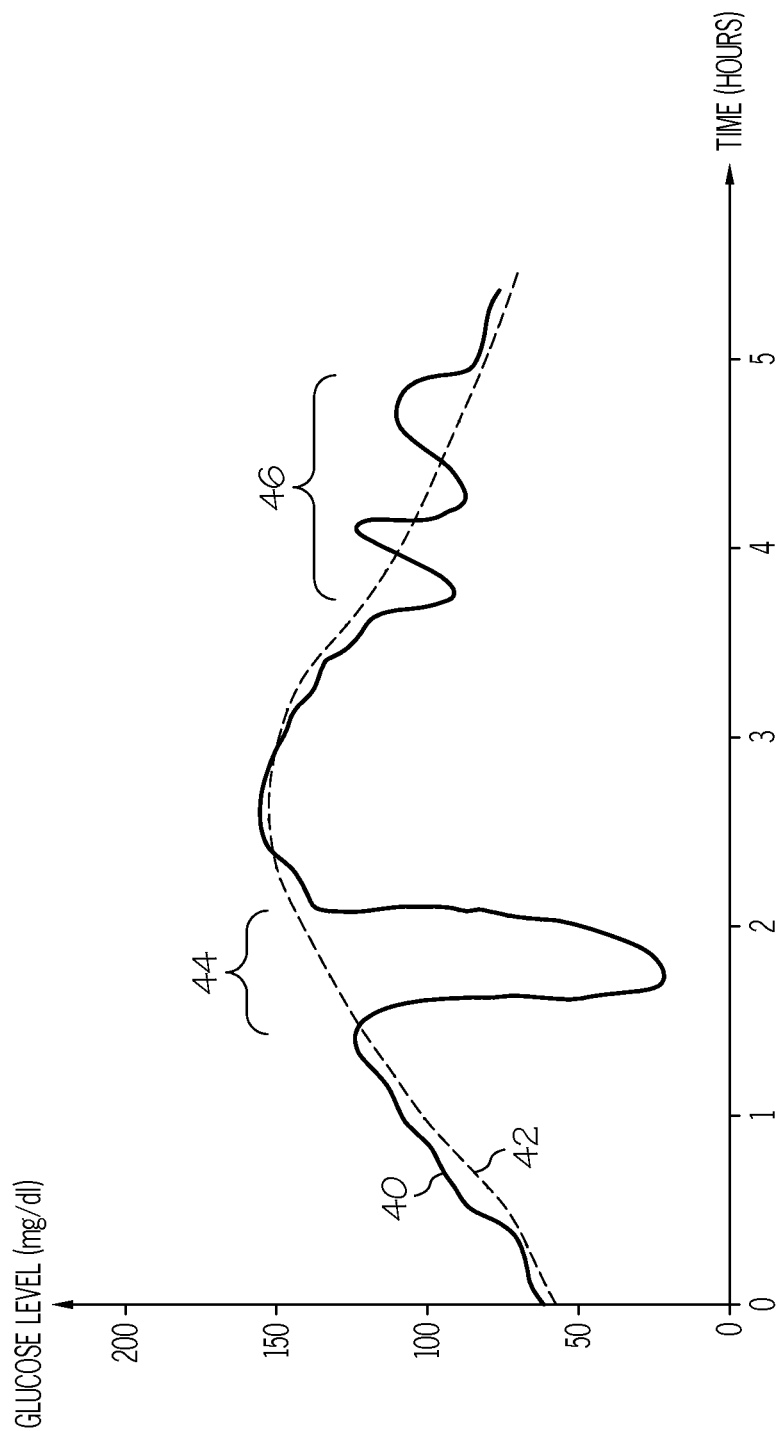
FIG. 3 depicts a graph of measured glucose results and actual glucose levels of the person according to one or more embodiments shown and described herein.

FIG. 3 depicts an example of a two-dimensional graph of measured glucose results 40 from a glucose sensor coupled to a person having diabetes. The horizontal axis represents time in hours, while the vertical axis represents the measured and actual glucose level of the person in milligrams of glucose per deciliter of blood (mg/dl). Measurements may be automatically taken by the glucose sensor at a predetermined rate, such as every one minute. The measured glucose results 40 may generally correspond to the actual glucose level 42 of the person. However, the glucose sensor may malfunction from time to time, as shown during time period 44 in FIG. 3. The malfunction may be due to sensor dropout caused by physiological problems near the glucose sensor's needle, or it may be due to electrical problems with the glucose sensor itself. During the malfunction time period 44, the measured glucose results 40 may be substantially lower than the actual glucose level 42 of the person. At the conclusion of the malfunction time period 44, the measured glucose results 40 may recover such that they again correspond to the actual glucose level 42 of the person.

Referring still to FIG. 3, the glucose sensor may also exhibit noise from time to time, as shown during time period 46. The noise may be due to physical movement of the glucose sensor's needle relative to the skin or may be due to electrical noise inherent in the glucose sensor itself. During the noise time period 46, the measured glucose results 40 may vacillate, such that some results are above and some are below the actual glucose level 42. The noise may even appear to oscillate about the actual glucose level 42. At the conclusion of the noise time period 46, the measured glucose results 40 may recover such that they again closely correspond to the actual glucose level 42 of the person. Although shown as occurring at different times, malfunction and noise may occur at the same time as well as consecutively. Furthermore, the duration of the malfunction and/or noise may be shorter or longer than as depicted in FIG. 3.

Figure 4:
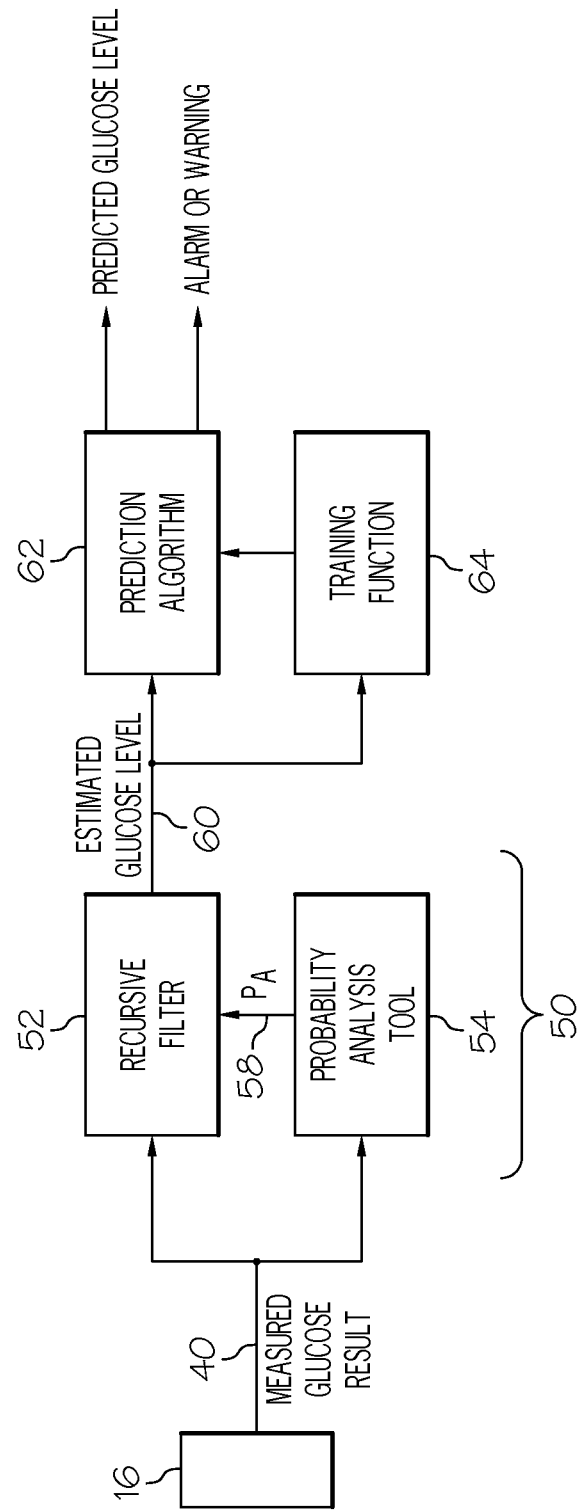
FIG. 4 depicts a probability analysis tool and a recursive filter according to one or more embodiments shown and described herein.

It is against the above background that embodiments according to the present disclosure are provided which estimate the person's actual glucose level in the presence of sensor noise and/or sensor malfunction. FIG. 4 depicts a system 50 configured to estimate the glucose level of the person. The system 50 may receive the measured glucose results 40 from a glucose sensor 16 which may be coupled to a person having diabetes (not shown). The glucose sensor 16 may be coupled to the person as previously described herein or in any suitable fashion. The glucose sensor 16 may be configured to periodically measure the glucose level of the person, such as for example every one minute, and transmit the measured glucose results 40 to the system 50 (e.g., via a communication link as described hereinbefore).

The system 50 for estimating the glucose level of a person having diabetes may comprise a probability analysis tool 54 and a recursive filter 52. The probability analysis tool 54 may be configured to receive the measured glucose results 40 and calculate the probability of glucose sensor accuracy $P_A$ 58, i.e., the probability that that glucose sensor 16 is functioning normally (i.e., not malfunctioning). The probability of glucose sensor accuracy $P_A$ 58 may be based solely on observable data, such as the measured glucose results 40 and/or changes thereof. Accordingly, the probability analysis tool 54 may be used to distinguish between sensor noise, which may have a normal distribution, and sensor malfunction which may not be normally distributed. Each type of uncertainty may be handled differently due to the differences in their uncertainty distributions.

The probability analysis tool 54 may comprise any number of mathematical algorithms which are capable of analyzing the measured glucose results 40 and/or changes thereof and calculating a probability of glucose sensor accuracy $P_A$ 58. The probability analysis tool 54 may be also configured to receive other types of data on which the probability of glucose sensor accuracy $P_A$ 58 may be based, such as when the person eats a meal, when the person exercises, and when insulin is delivered to the person. In addition, $P_A$ 58 may be based on one or more measurements from an impedance measuring device coupled to the person and configured to measure impedance in the person. Such an impedance measuring device may indicate whether the glucose sensor 16 is properly coupled to the person and, thus, whether the measured glucose results 40 from the glucose sensor 16 are accurate. Other types of data may be used as well.

The probability analysis tool 54 can be take on a number of different forms such as a state machine, Bayesian models, or other algorithms. In one embodiment, the probability analysis tool 54 may take the form of a simple state machine, in which the probability of glucose sensor accuracy $P_A$ may always be in the set $\{0,1\}$ (i.e., $P_{A\,58\,is\,either}$ 0% or 100%, depending on the state of the state machine). In this example, the system would transfer to a state of sensor inaccuracy, $T_{A \to I}$, if the $\Delta CG$ (i.e., the change in the current measured glucose result from the previous measured glucose result) is less than a certain negative threshold, $\tau_1$, and transfer back to a state of sensor accuracy, $T_{I \to A}$, if the $\Delta CG$ is greater than a certain positive threshold, $\tau_2$, or if the sensor CG value (i.e., the current measured glucose result) are within physiologically possible glucose values ($g_0$ and $g_{max}$) and a certain amount of time has elapsed since the transition to the state of sensor inaccuracy, $\Delta t_{A \to I} > \tau_3$. This may be represented mathematically as:

$T_{A \to I}$ if $\Delta CG < \tau_1$ $T_{I \to A}$ if $\Delta CG > \tau_2$ or ($g_0 < CG < g_{max}$ and $\Delta t_{A \to I} > \tau_3$)

If neither of these transfer conditions are met, then the state machine may remain in its current state. This is just one example of the probability analysis tool 54 taking the form of a state machine. The probability analysis tool 54 may take on other forms as well.

In another embodiment, the probability analysis tool 54 may comprise a hidden Markov model having two states for the glucose sensor: 1) The state wherein the glucose sensor is accurate, denoted by "$S_A$", and 2) The state wherein sensor is inaccurate, denoted by "$S_I$". The hidden Markov model may provide state transition functions that define the probability of transitioning from state $S_A$ to state $S_I$, such as the following function:

$$P_{A \to I} = \min\left[\left(1 - \frac{1}{1 + e^{-(\Delta CG + \alpha_1)/\alpha_2}}\right) + \left(1 - \frac{1}{1 + e^{-(CG + \alpha_3)/\alpha_4}}\right), 1\right],$$

where "CG" is the current measured glucose result, "$\Delta CG$" is the change from the previous measured glucose result to the current measured glucose result, and $\alpha_1$ to $\alpha_4$ are constants which depend on the characteristics of the glucose sensor. The range of output values for this function are zero to one, where zero represents 0% probability and one represents 100% probability of sensor accuracy. The "min" function takes the minimum value of the mathematical expression and the number one (i.e., 100%). This transition function may be based on the current CG and $\Delta CG$ values. Furthermore, the transition function may be a sigmoid, wherein the parameters $\alpha_1$ and $\alpha_3$ control the location of the sigmoid transition, and parameters $\alpha_2$ and $\alpha_4$ control the slope of the sigmoid. These parameters may be tuned for a specific patient and/or sensor batch.

Continuing with the example of the hidden Markov model, the probability of remaining in state $S_I$ (when the current state is $S_I$) may be $$P_{I \to I} = \max\left[\gamma P_{I_{k-1}}\left(\frac{1}{1 + e^{-(\Delta CG + \alpha_5)/\alpha_6}}\right), 0\right]$$

and is only a function of the $\Delta CG$ value and the previous probability $P_{I_{k-1}}$ of being in or transitioning to state $S_I$. The range of output values for this function are zero to one, where zero represents 0% probability and one represents 100% probability. The "max" function takes the maximum value of the mathematical expression and the number zero (i.e., 0%). The parameter "γ" is a decay term that is less than one and designed to gradually transition the state of the hidden Markov model back to $S_A$ if there is no evidence from the CG and ΔCG values to remain in $S_I$. The parameter γ may be a constant and may be related to the probability of remaining in $S_I$ when ΔCG is relatively normal. For example, γ may be selected so that the hidden Markov model remains in $S_I$ for approximately 10 minutes when ΔCG is relatively normal. This probability function also includes a sigmoid function that detects rapid rises in the CG signal that are associated with a return to $S_A$. The parameter $\alpha_5$ controls the location of the sigmoid transition, and parameter $\alpha_6$ controls the slope of the sigmoid. Both of these parameters may be tuned for a specific patient and/or sensor batch.

The current probability $P_I$ of transitioning to $S_I$ is either $P_{A \to I}$ or $P_{I \to I}$, depending on whether the current state is $S_A$ or $S_I$. The current probability $P_I$ of the glucose sensor being inaccurate (i.e., being is $S_I$) may be $(S_A \times P_{A \to I}) + (S_I \times P_{I \to I})$. Note that the state ($S_A$ or $S_I$) is "1" when in that state and "0" otherwise. This includes the probability of transitioning to $S_I$ ($P_{A \to I}$) given the probability of being in $S_A$, and the probability of remaining in $S_I$ times the probability of currently being in $S_I$. The value of $P_{I \to I}$ is equal to $1-P_{I \to A}$, and the probability of the sensor being accurate is simply $P_A=1-P_I$. Thus, for this example, the probability of glucose sensor accuracy may be $P_A=1-[(S_A \times P_{A \to I})+(S_I \times P_{I \to I})]$.

Figure 5:
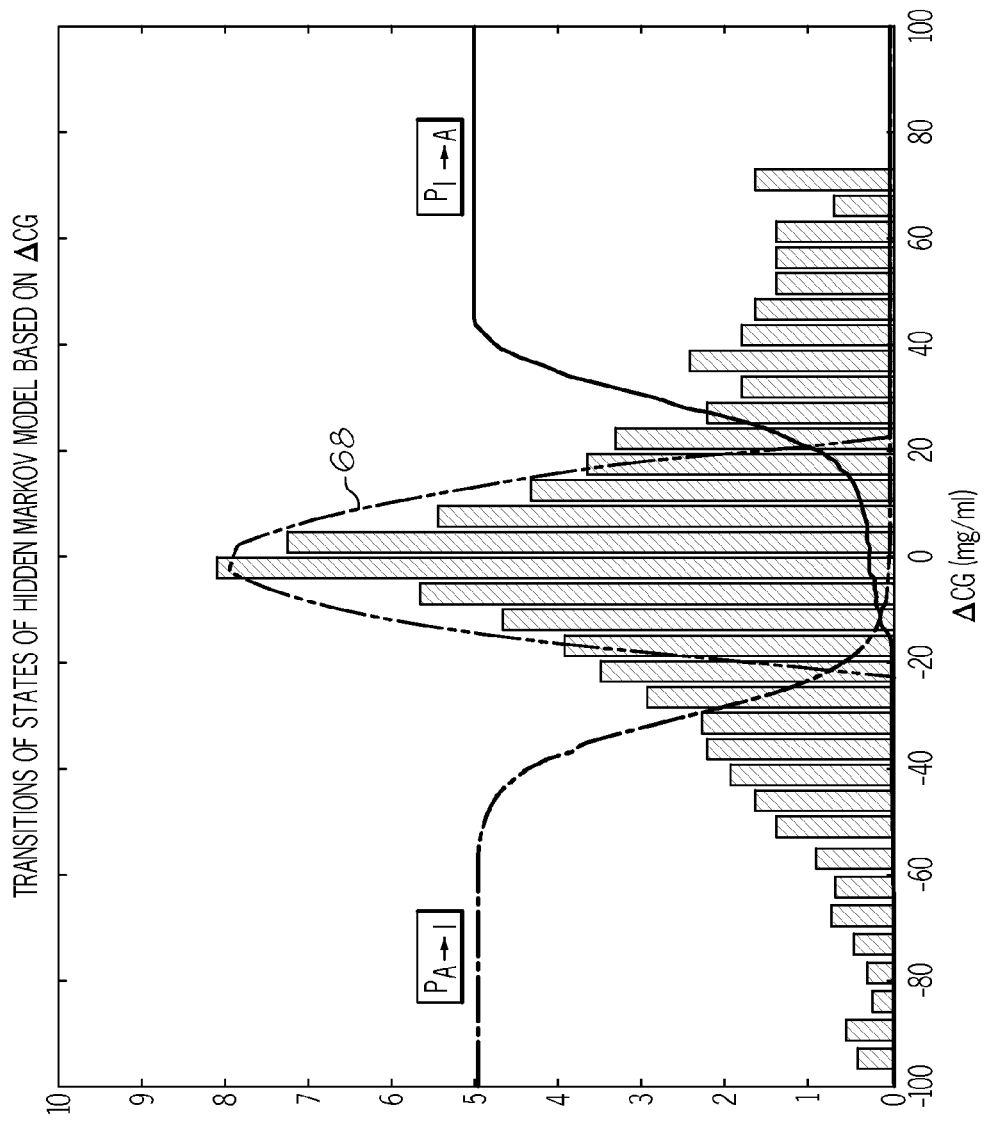
FIG. 5 depicts state transitions for the hidden Markov model according to one or more embodiments shown and described herein.

FIG. 5 depicts a graphical representation of the two transition functions, $P_{A \to I}$ and $P_{I \to A}$ (i.e., $1-P_{I \to I}$, the probability of transitioning from $S_I$ to $S_A$ when the current state is $S_I$), over a histogram of ΔCG. The histogram includes a Gaussian-shaped component 68 centered about zero with two tails associated with the transitions in and out of sensor malfunction. The two transition functions are plotted over the histogram to show that they may be tuned to trigger on the tails of the histogram. The Gaussian-shaped component 68 may represent the range of ΔCG values which may occur during normal operation of the glucose sensor. The ΔCG values located inside the Gaussian-shaped component 68 may be due to sensor noise, for example. The ΔCG values located outside and to the left of the Gaussian-shaped component 68 may be due to sensor transitioning from $S_A$ to $S_I$. The shape of this distribution may be used to characterize a batch of glucose sensors after production and used to code the sensors. That is, the transition functions ($P_{A \to I}$ and $P_{I \to I}$) may be adjusted (by adjusting $\alpha_1$ to $\alpha_6$ parameters) to correspond to the Gaussian-shaped component 68 for a particular batch of glucose sensors. Thus, the hidden Markov model may be used to determine the probability of sensor being accurate, $P_A$, based solely on the measured glucose results and changes thereof.

Figure 6:
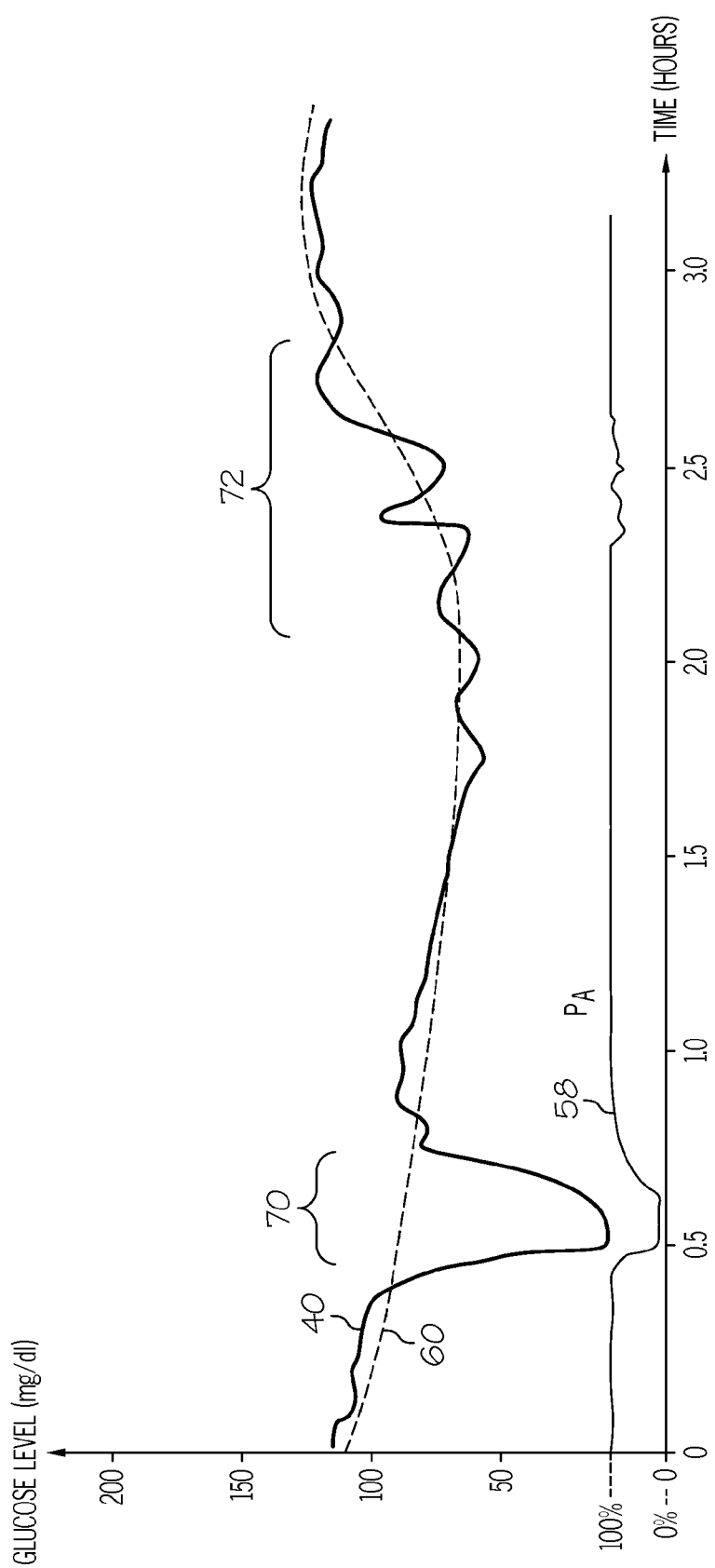
FIG. 6 depicts the operation of a hidden Markov model and a Kalman filter according to one or more embodiments shown and described herein.

FIG. 6 illustrates a graph which shows an example of the operation of the hidden Markov model during glucose sensor malfunction and in the presence of glucose sensor noise. The graph includes the measured glucose results 40 and the probability of glucose sensor accuracy, $P_A$ 58. During time period 70, the glucose sensor may malfunction, thus causing the measured glucose results 40 to become inaccurate; at the same time, $P_A$ 58 (as determined by the hidden Markov model) may decrease from approximately 100% (before time period 70) to near 0% during time period 70. This may be due to the hidden Markov model's detection of the rapid decline in the value of the measured glucose results 40 at the beginning of time period 70 (i.e., when the malfunction first occurs). At the end of time period 70, the glucose sensor may begin to operate normally (i.e., the measured glucose results 40 become accurate again) and $P_A$ 58 may increase back to approximately 100% again. As before, this may be due to the hidden Markov model's detection of the rapid increase in the value of the measured glucose results 40 at the end of time period 70 (i.e., when the glucose sensor returns to normal operation). The rate of change of $P_A$ 58 from near 0% to approximately 100% may depend on how quickly the glucose sensor transitions from malfunctioning (inaccurate) to normal (accurate) operation. If the transition is relatively fast, $P_A$ 58 may transition quickly from near 100% to approximately 0%. However, if the glucose sensor transitions slowly from malfunctioning to normal operation, $P_A$ 58 may also transition slowly from near 0% to approximately 100%. The decay term γ (found in the $P_{I \to I}$ equation) may permit $P_A$ 58 to gradually transition back to $S_A$ if there is little or no evidence from the CG and ΔCG values to remain in $S_I$.

Referring still to FIG. 6, glucose sensor noise, which is shown as occurring during time period 72, may also cause $P_A$ 58 to decrease, depending on the severity and level of the noise. As depicted in FIG. 6, the glucose sensor noise during time period 72 may cause $P_A$ 58 to decrease slightly. Of course, both glucose sensor malfunction and sensor noise may have varying levels of amplitude and/or duration. Furthermore, glucose sensor malfunction and sensor noise may temporally overlap, either in part or completely. The hidden Markov model may be configured to determine $P_A$ 58 under any of these conditions. As will be discussed hereinafter, $P_A$ 58 may be used in a recursive filter in order to minimize the effect of glucose sensor malfunction so as to provide an accurate estimate the actual glucose level of the person in the presence of glucose sensor malfunction and/or sensor noise.

Referring again to FIG. 4, the system 50 for estimating the glucose level of a person having diabetes may comprise a recursive filter 52 which may be used to estimate the glucose level of the person, based on the plurality of measured glucose results weighted with the probability of glucose sensor accuracy $P_A$ 58. Examples of recursive filters which may be used include a Kalman filter and an Extended Kalman filter (EKF). Of course many other types of recursive filters may be used as well.

In one embodiment, the recursive filter 52 may be a Kalman filter (hereinafter references to a "Kalman filter" also apply to an "Extended Kalman filter") which is configured to process the measured glucose results 40 (i.e., the raw glucose sensor data) in a second-order linear system, as embodied in the equations below. The Kalman filter may comprise inter alia a state vector which represents the estimated state of the variable being estimated, which in this example is the glucose level of the person. The Kalman filter may include a prediction step, in which an a priori state and covariance are predicted, as wells as a measurement step, in which the a posteriori Kalman gain ($K_k$), the state vector, and the covariance are updated. The state vector may be updated every time a new input is received (i.e., recursively). In this disclosure, the variables in the state vector x may represent an estimate of the person's actual glucose level, based on the measured glucose results 40. The estimated glucose level vector, x, may represent the estimated glucose level of the person, g; its first derivative, ġ; and its second derivative, g̈. The measured glucose results vector, z, may include the current CG and ΔCG values. Other dynamic models may be used as well. The vectors x and z may be represented as $x_k=[g\ \dot{g}\ \ddot{g}]^T$ and $z_k=[CG\ \Delta CG]^T$, where k represents kth sample. The following equation may be used to estimate the glucose level vector, x: $x_k=\hat{x}_k+K_k(z_k-H\hat{x}_k)P_A$, where k represents the kth sample, $\hat{x}_k=Ax_{k-1}$, $K_k$ is the Kalman gain, and $P_A$ 58 is the probability of glucose sensor accuracy (from the probability analysis tool). In this fashion, the probability of sensor accuracy $P_A$ 58 may be used to weight the measured glucose results, embodied in the matrix $z_k$. The matrices and supporting equations for the Kalman filter may be as follows:

$$A = \begin{bmatrix} 1 & 1 & 0 \\ 0 & \beta_1 & 1 \\ 0 & 0 & \beta_2 \end{bmatrix},$$

$$Q = \begin{bmatrix} \sigma_g^2 & 0 & 0 \\ 0 & \sigma_g^2 & 0 \\ 0 & 0 & \sigma_g^2 \end{bmatrix},$$

$$H = \begin{bmatrix} 1 & 0 & 0 \\ 0 & 1 & 0 \end{bmatrix},$$

$$\hat{P}_k = A P_{k-1} A^T + Q_{k-1},$$

$$K_k = \hat{P}_k H^T (H \hat{P}_k H^T + R_k)^{-1},$$

$$P_k = (I - K_k H) \hat{P}_k,$$

$$R_k = \min\left[\sum_{i=1}^{\tau} \frac{(C_{k-i} - \overline{C})^2}{\tau - 1} + P_D \sigma_{max}^2, \sigma_{max}^2\right] + \sigma_{CG}^2,$$

$$C_{k-i} = CG_{k-i} - H x_{k-i},$$

and $$\overline{C} = \frac{1}{\tau} \sum_{i=1}^{\tau} C_{k-i}.$$

The parameters $\beta_1$ and $\beta_2$ in matrix A may be set to slightly less than one so that the estimated glucose level is damped when sensor malfunction occurs. The matrix Q may represent the process noise covariance, while $K_k$ may represent the Kalman filter gain. Initial estimates for these parameters may be determined as is known in the art.

In the Extended Kalman filter (EKF), the system may be represented with a nonlinear model, $\hat{x}_k = f(x_{k-1}, u_k)$, and measurements are also represented with a nonlinear model, $z_k = h(x_k)$. This nonlinear model may include inputs from other sources, $u_k$, that may include meals, insulin, exercise or other inputs that may affect the glucose model. The nonlinear model may be derived from proprietary glucose physiological models. The prediction step is done by evaluating the nonlinear model, and the predicted uncertainty is calculated using the Jacobian of the model, $F_k$, with the state vector. This creates a localized linear model about the current system state. The following equations may be used by the EKF:

$$F_k = \begin{bmatrix} \frac{\partial f_1}{\partial x_1} & \cdots & \frac{\partial f_1}{\partial x_N} \\ \vdots & \ddots & \vdots \\ \frac{\partial f_N}{\partial x_1} & \cdots & \frac{\partial f_N}{\partial x_N} \end{bmatrix}$$

$$H_k = \begin{bmatrix} \frac{\partial h_1}{\partial x_1} & \cdots & \frac{\partial h_1}{\partial x_N} \\ \vdots & \ddots & \vdots \\ \frac{\partial h_M}{\partial x_1} & \cdots & \frac{\partial h_M}{\partial x_N} \end{bmatrix}$$

$$\hat{x}_k = f(x_{k-1}, u_k)$$

$$\hat{P}_k = F_k P_{k-1} F_k^T + Q_{k-1}$$

-continued $$K_k = \hat{P}_k H_k^T (H_k \hat{P}_k H_k^T + R_k)^{-1}$$

$$P_k = (I - K_k H_k) \hat{P}_k$$

$$x_k = \hat{x}_k + K_k (z_k - h(\hat{x}_k)) P_A.$$

After the prediction step, the current glucose sensor measurement, $CG_k$ may be used in the correction step. The correction step may also include the previously calculated probability of glucose sensor accuracy, $P_A$ 58 (from the probability analysis tool). The Kalman filter may be configured to weight the current measured glucose result with the probability of glucose sensor accuracy. For example, when $P_A$ 58 is low, the impact of the current measured glucose result on the Kalman filter may approach zero; conversely, when $P_A$ 58 is high, the impact of the current measured glucose result may be higher. Using $P_A$ 58 in this fashion may be a logical modification to the operation of the Kalman filter because, when sensor malfunction occurs, the current measured glucose results likely provide little or no useful information regarding the actual glucose level of the person.

Distinguishing between sensor malfunction and sensor noise may facilitate estimating the glucose level of the person, and, as such, the Kalman filter may treat them differently. For normally distributed sensor noise, the Kalman filter may be configured to average out such noise. This may be due to the fact that sensor noise may be characterized for each type and/or batch of glucose sensors, including but not limited to the frequency range of the noise and the corresponding range of amplitude changes in the measured glucose results. These noise characteristics may be embodied in some or all of the parameters of the Kalman filter (e.g., in $\sigma_{max}^2$ or $\sigma_{CG}^2$) such that the Kalman filter is configured to filter out the noise and provide a relatively accurate estimated glucose level of the person, even in the presence of the sensor noise. On the other hand, sensor malfunction error is generally not normally distributed, so it should be handled differently within the Kalman filter framework. In one embodiment of the Kalman filter, $P_A$ 58 (determined by the probability analysis tool) may be used by the Kalman filter to weight the measured glucose results such that, when sensor malfunction occurs, the measured glucose results are largely ignored.

An example of the operation of a Kalman filter is shown in FIG. 6, which depicts the measured glucose results 40 and the estimated glucose level 60 of the person. As previously discussed, the probability of glucose sensor accuracy, $P_A$ 58, is shown as well. Normally, the person's estimated glucose level 60 may generally follow the measured glucose results 40. However, during time period 70, the sensor may malfunction; at the same time, $P_A$ 58 may decrease to near 0% (as determined by the operation of the probability analysis tool) so as to indicate a low probability of glucose sensor accuracy. Accordingly, the Kalman filter may take into account $P_A$ 58 so as to lessen the importance of the measured glucose results in estimating the glucose level of the person during the time period 70 of the sensor malfunction.

Continuing to refer to FIG. 6, the measured glucose results 40 may contain noise during time period 72. The Kalman filter may filter this noise so as to produce an estimated glucose level 60 which is relatively smooth during this time period 72. Although the measured glucose results may contain noise during time period 72, $P_A$ 58 may remain relatively high (e.g., near 100%) during this time since the probability analysis tool may be able to discern between sensor noise and sensor malfunction. As such, the Kalman filter may continue to place a relatively high importance on the measured glucose results during time period 72 (as evidenced by $P_A$ 58 being relatively high during time period 72).

The glucose sensor measurement uncertainty, $R_k$, is generally not constant. It may currently be estimated as a function of recent sensor measurements, z; the probability of glucose sensor accuracy, $P_A$; the maximum uncertainty of the measurement, $\sigma_{max}^2$; and the normal uncertainty associated with continuous glucose measurements, $\sigma_{CG}^2$. $\sigma_{max}$ may be calculated as the maximum physiological variance for glucose in a person with poorly controlled diabetes. It may be estimated from samples of CGM data. Similarly, $\sigma_{CG}$ is the minimal uncertainty for a glucose sensor when working properly. It may be the best case performance for a sensor and may be estimated by the variance of the measured glucose results compared to finger-stick data when the sensor is performing ideally. There may be other methods for estimating the measurement uncertainty that include using higher frequency glucose sensor data. This may be interpreted as the variance of the difference between recent past CG measurements and the estimated Kalman filter state.

The estimated glucose level of the person, as determined by the recursive filter, may be used to predict the glucose level of the person at some time in the future. These estimates may also be used to analyze the person's behavior and glucose patterns. Referring back to FIG. 4, a prediction algorithm 62 may be used to predict whether and/or when the person may become hypoglycemic and may provide associated alarms or warnings. The prediction algorithm 62 may receive the person's estimated glucose level 60 from the recursive filter 52 and may also receive the uncertainty of the estimated glucose level. However, the prediction algorithm 62 may be augmented with other input data, including meal times, carbohydrates, medications, exercise, insulin doses, and so forth. The prediction algorithm 62 may further receive information from other sources of data as well such as the measured glucose results (i.e., the raw glucose sensor data) or processed glucose sensor data. The prediction algorithm 62 may use Gaussian Process regression to learn a patient specific prediction model, indicated by the training model 64 in FIG. 4. The prediction algorithm 62 may also estimate the uncertainty of the prediction, which may allow the alarm thresholds to be adjusted for sensitivity. The alarm thresholds may also be adjusted based on the patient's current activity; for example, the sensitivity could be increased when the patient is sleeping.

As an example, the prediction of hypoglycemia can be done using the system model of the Kalman filter or the Extended Kalman filter. In this example the prediction step, $\hat{x}_k = Ax_{k-1}$ or $\hat{x}_k = f(x_{k-1}, u_k)$, is iterated for the desired prediction time and the predicted value is compared to the specific threshold. For example, if Kalman filter is updated every one minute, the prediction step may iterate the Kalman filter forty-five times in order to predict the glucose level of the person from the present to forty-five minutes in the future. The prediction model may include additional predicted inputs such as anticipated meals, insulin, exercise, or other anticipated future inputs.

In another example, the estimated glucose value, g, and rate-of-change of the glucose value, ġ, as estimated by the recursive filter are used to define a linear forecast which is compared to the hypoglycemia threshold. The forecast is done with the following equation by multiplying the derivative by the desired prediction time, $t_{pr}$, to calculate the predicted glucose value, ĝ.

$$\hat{g} = g + \dot{g} t_{pr}.$$

As an example, the specific input vectors used may include three samples of the estimated glucose levels (CG) taken at time t=0, −15, and −30 minutes, the current derivative of the estimated glucose level and the derivative at t=−15 minutes, and the time since the last meal. The meal information, $t_{meal}$, and bolus information, B, are optional and other data can also be included. This may be expressed mathematically as $$x_{CG} = [CG_{t=0}\ CG_{t=-15}\ CG_{t=-30}\ \Delta CG_{t=0\ldots-15}\ \Delta CG_{t=-15\ldots-30}]^T$$

$$x_{meal} = [CG_{t=0}\ CG_{t=-15}\ CG_{t=-30}\ \Delta CG_{t=0\ldots-15}\ \Delta CG_{t=-15\ldots-30}\ \min(t_{meal}, t_{max})\ B]^T$$

Gaussian process regression may use the following equation to predict future glucose levels of the person based on training data, represented by (X,y), and the test point (x*,y*):

$$y^* = k(x^*, X)(k(X,X) + \mu I)^{-1} y,$$

where k(x,x) is a covariance function. A Gaussian covariance function may be used to generate the results, but other functions can be used here as well. A Gaussian covariance function which may be used is:

$$k(\hat{x}, x) = \exp\left[-\frac{1}{2\sigma_k^2} \|\hat{x} - x\|^2\right].$$

Figure 7:
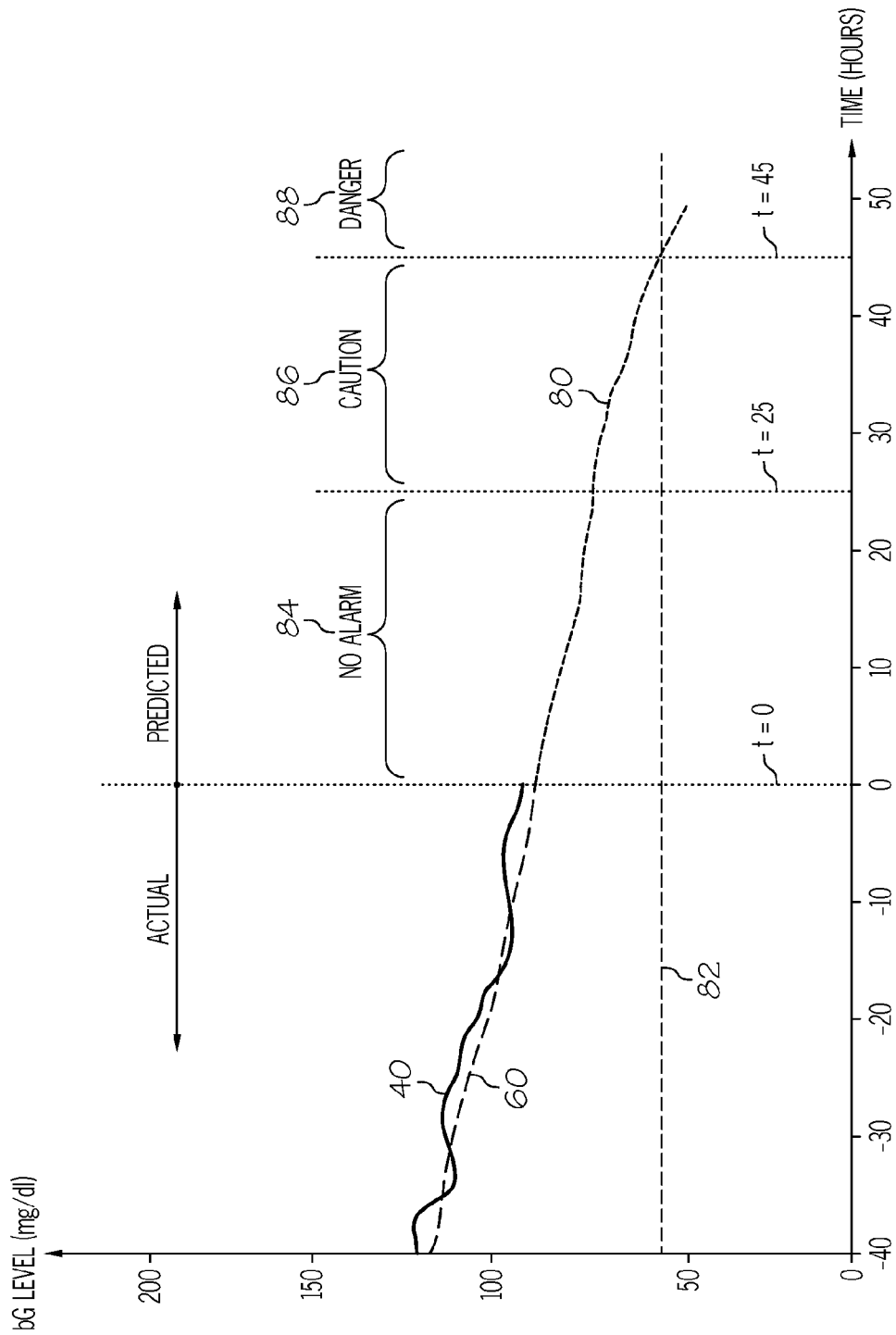
FIG. 7 depicts the operation of a prediction algorithm according to one or more embodiments shown and described herein.

FIG. 7 depicts the operation of the prediction algorithm. The measured glucose results 40 from the glucose sensor, and the estimated glucose level 60 of the person (i.e., the output of the Kalman filter) are shown on the left (from a time t=−40 to 0). The current time is t=0. The prediction algorithm may determine the person's predicted glucose level 80 at some time in the future (i.e., any time greater than t=0). Furthermore, the prediction algorithm may be used to predict whether and/or when the glucose level of the person may become hypoglycemic. A hypoglycemic threshold 82 may be established for the person, such that an actual glucose level below this threshold means the person has become hypoglycemic. The hypoglycemic threshold 82 may be uniquely determined for each person. The threshold for an average person may be about 50 mg/ml. Also the hypoglycemic threshold 82 may vary for each person, such that the threshold is based on time, on an event, or combinations thereof. As examples, the hypoglycemic threshold 82 for a person may depend on the time of day, whether the person has taken medication, whether and/or how long the glucose sensor is in the dropout state, and so forth. The prediction algorithm may be able to predict when the person may become hypoglycemic. In FIG. 7, the prediction algorithm may predict that the person will become hypoglycemic at t=45 (i.e., 45 minutes from the current time). Of course, as time progresses, the prediction algorithm may continue to use the latest estimated glucose level (from the Kalman filter) and adjust the predicted glucose levels accordingly.

In addition to being able to predict future values of the glucose level of the person, the prediction algorithm may be further configured to determine the probability that the prediction is accurate. For example, predictions only one or two minutes in the future may be highly accurate, while predictions which are 60 or 70 minutes in the future may be relatively inaccurate. Of course the probability that the prediction is accurate may be a continuum, starting at near 100% for the immediate future and decaying to near 0% as the prediction reaches further into the future. This information may be used, in conjunction with the actual prediction itself, to provide a hypoglycemia warning system for the person. As shown in FIG. 7, the warning system may provide no alarm 84 when the predicted glucose level 80 is sufficient high above the hypoglycemic threshold 82; it may advise caution 86 when the predicted glucose level 80 approaches within a predetermined range of the hypoglycemic threshold 82; and it may advise danger 88 when the predicted glucose level 80 drops below the hypoglycemic threshold 82.

The prediction algorithm, as previously discussed, may include a training function which learns the specific characteristics of a person. The training function may produce training data which may be used in the prediction algorithm and may be weighted based on the influence they have on generating the prediction. The level of influence the training data may be determined by the covariance function k(x,x) used within the Gaussian Process regressor.

The prediction algorithm may be initialized with a generic set of training examples or no training examples. As new data are measured they may be incorporated into the prediction algorithm and/or training function. There are many possible algorithms for including new data. These include adding the data to the training set when 1) A predetermined period of time has elapsed, 2) The prediction failed on the specific data, 3) The input data is not represented in the training set, or 4) A patient or care provider manually includes the data, including all new data, if suitable.

Figure 8:
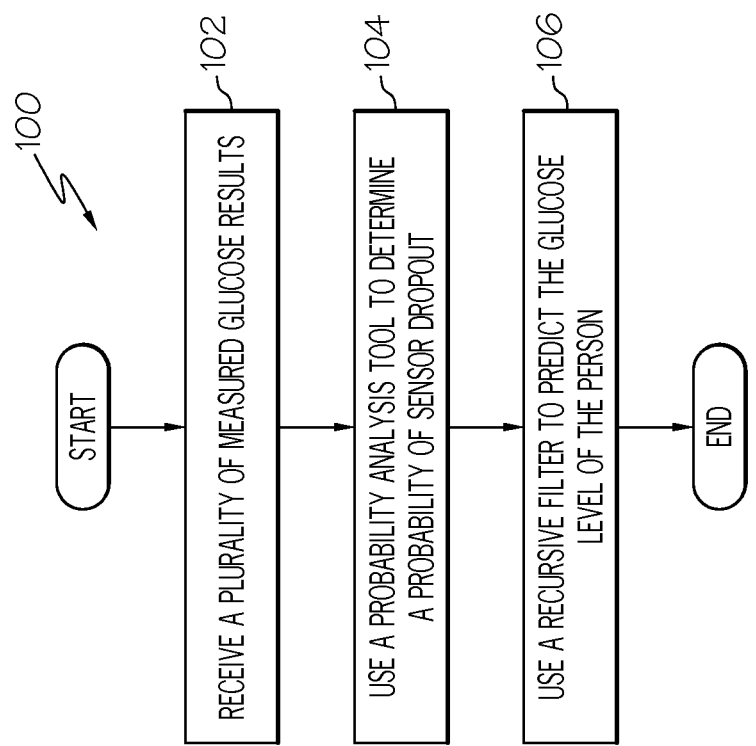
FIG. 8 depicts a method of predicting the glucose level of the person using a probability analysis tool and a recursive filter according to one or more embodiments shown and described herein.

When added to the training set, the new data can be included as a new vector, or by reweighing an existing training vector. The second method includes the benefit of maintaining constant memory needs. After adding additional data, the prediction algorithm may be updated immediately on the device, retrospectively on a personal computer, or retrospectively at a clinic Referring to FIG. 8, a method 100 is shown for estimating a glucose level of a person having diabetes. The method may comprise a number of acts, which may be performed in any suitable order. At act 102, the method 100 may receive into a computing device a plurality of measured glucose results from a glucose sensor coupled to the person. At act 104, the method 100 may use the computing device to analyze the plurality of measured glucose results with a probability analysis tool configured to determine a probability of glucose sensor accuracy based on the plurality of glucose measurements. And at act 106, the method 100 may use the computing device to estimate a glucose level of the person using a recursive filter configured to weight the plurality of measured glucose results with the probability glucose sensor accuracy. The probability analysis tool and the recursive filter may be established as described hereinabove.

It should now be understood that the methods and systems described herein may be used to estimate the glucose level of a person having diabetes, even in the presence of noise and/or sensor inaccuracy (e.g., sensor dropout). Furthermore, the methods and systems described herein may also be used to predict the future glucose level of the person. As such, they may be able to predict whether and/or when the person's glucose level may become hypoglycemic. Upon detecting or predicting that the person may become hypoglycemic, the methods and systems may provide corresponding information to the person, such as for example a warning. The methods described herein may be stored on a computer-readable medium which has computer-executable instructions for performing the methods. Such computer-readable media may include compact discs, hard drives, thumb drives, random-access memory, dynamic random-access memory, flash memory, and so forth.

It is noted that recitations herein of a component of the present disclosure being "configured" in a particular way, "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

While particular embodiments and aspects of the present invention have been illustrated and described herein, various other changes and modifications may be made without departing from the spirit and scope of the invention. Moreover, although various inventive aspects have been described herein, such aspects need not be utilized in combination. It is therefore intended that the appended claims cover all such changes and modifications that are within the scope of this invention.

What is claimed is:

1. A method for estimating a glucose level of a person having diabetes, the method comprising:
   receiving into a computing device a plurality of measured glucose results from a glucose sensor coupled to the person;
   using the computing device to analyze the plurality of measured glucose results with a probability analysis tool configured to determine a probability of glucose sensor accuracy $P_A$ based on the plurality of measured glucose results;
   using the computing device to estimate the glucose level of the person with a recursive filter configured to estimate the glucose level based on the plurality of measured glucose results weighted with the probability of glucose sensor accuracy $P_A$; and
   wherein the probability analysis tool comprises a hidden Markov model, wherein:
   the hidden Markov model has two states:
      a first state $S_A$ indicating the glucose sensor is accurate, and
      a second state $S_I$ indicating the glucose sensor is inaccurate; and
   the hidden Markov model is configured to determine the probability of glucose sensor accuracy $P_A$, based on a state of the hidden Markov model and the plurality of measured glucose results; and
   wherein probability of the hidden Markov model transitioning from the first state $S_A$ to second the state $S_I$ is $$P_{A \to I} = \min\left[\left(1 - \frac{1}{1 + e^{-(\Delta CG + \alpha_1)/\alpha_2}}\right) + \left(1 - \frac{1}{1 + e^{-(CG + \alpha_3)/\alpha_4}}\right), 1\right],$$

where CG is a most-recent measured glucose result, $\Delta CG$ is a most-recent change in the plurality of measured glucose results, and $\alpha_1, \alpha_2, \alpha_3$ and $\alpha_4$ are constants related to characteristics of the glucose sensor.

2. The method of claim 1, wherein the computing device comprises a blood glucose meter, an insulin pump, a microprocessor coupled to the glucose sensor, a cellular phone, a smart phone, a personal digital assistant, a personal computer, or a computer server.

3. The method of claim 1, wherein the glucose sensor comprises a continuous glucose monitoring system physically coupled to the person having diabetes and configured to automatically measure the glucose level of the person.

4. The method of claim 1, wherein the plurality of measured glucose results comprises periodic glucose measurements taken approximately every one minute.

5. The method of claim 1, wherein the probability analysis tool is configured to determine a probability of glucose sensor accuracy $P_A$ further based on at least one of:
- when the person eats a meal;
- when the person exercises;
- when insulin is delivered to the person; and
- one or more measurements from an impedance measuring device coupled to the person having diabetes and configured to measure impedance in the person.

6. The method of claim 1, wherein probability of the glucose sensor being in the second state $S_I$ is based on a most-recent measured glucose result, a most-recent change in the plurality of measured glucose results, or a combination thereof.

7. The method of claim 1, wherein probability of the hidden Markov model remaining in the second state $S_I$ is $$P_{I \to I} = \min\left[\gamma P_{I_{k-1}} - \left(\frac{1}{1+e^{-(\Delta CG + \alpha_5)/\alpha_6}}\right), 0\right],$$

where $\Delta CG$ is a most-recent change in the plurality of measured glucose results, $P_{I_{k-1}}$ is a previous probability of transitioning to or being in the second state $S_I$, and $\gamma$, $\alpha_5$, and $\alpha_6$ are constants related to characteristics of the glucose sensor.

8. The method of claim 1, wherein the probability of glucose sensor accuracy $P_A$ is $1 - [(P_{A \to I} \times S_A) + (P_{I \to I} \times S_I)]$, wherein $S_A=1$ when the hidden Markov model is in the first state $S_A$ and $S_A=0$ otherwise,
$S_I=1$ when the hidden Markov model is in the second state $S_I$ and $S_I=0$ otherwise,
$P_{A \to I}$ is a probability of transitioning from the first state $S_A$ to the second state $S_I$, and
$P_{I \to I}$ is a probability of remaining in the second state $S_I$ when in the second state $S_I$.

9. The method of claim 1, wherein the recursive filter is a Kalman filter or an Extended Kalman filter.

10. The method of claim 9 further comprising using the computing device to predict a future glucose level of the person with the Kalman filter or the Extended Kalman filter, wherein:
- the Kalman filter or the Extended Kalman filter comprises a prediction step and a measurement step; and
- the prediction step is performed one or more times in order to predict the future glucose level of the person.

11. The method of claim 9, wherein the Kalman filter or the Extended Kalman filter comprises a state vector, $x_k = [g \ \dot{g} \ \ddot{g}]^T$, where k represents a kth sample of the state vector, g represents the estimated glucose level of the person, $\dot{g}$ represents a first derivative of g, and $\ddot{g}$ represents a second derivative of g.

12. The method of claim 11, wherein using the computing device to estimate the glucose level of the person comprises determining the state vector $x_k = \hat{x}_k + K_k(z_k - H\hat{x}_k)P_A,$ where $$\hat{x}_k = \begin{bmatrix} 1 & 1 & 0 \\ 0 & \beta_1 & 1 \\ 0 & 0 & \beta_2 \end{bmatrix} x_{k-1}, z_k = [CG \ \Delta CG]^T, H = \begin{bmatrix} 1 & 0 & 0 \\ 0 & 1 & 0 \end{bmatrix},$$

CG is a most-recent measured glucose result, $\Delta CG$ is a most-recent change in the plurality of measured glucose results, $K_k$ is a Kalman gain, $P_A$ is the probability of glucose sensor accuracy, and $\beta_1$ and $\beta_2$ are constants related to characteristics of the glucose sensor.

13. The method of claim 12, wherein the Kalman gain $K_k$ is based on a measurement uncertainty $R_k$ such that the measurement uncertainty $R_k$ is variable and is based on the probability of sensor accuracy.

14. The method of claim 13, wherein the measurement uncertainty $R_k$ is:

$$R_k = \min\left[\sum_{i=1}^{\tau} \frac{(C_{k-i} - \overline{C})^2}{\tau - 1} + P_I \sigma_{max}^2, \sigma_{max}^2\right] + \sigma_{CG}^2,$$

where $C_{k-i} = CG_{k-i} - Hx_{k-i}$, $\overline{C} = \frac{1}{\tau}\sum_{i=1}^{\tau} C_{k-i}$, $\tau$ represents a time history, $\sigma_{max}$ represents a maximum physiological variance for glucose in a person with poorly controlled diabetes, and $\sigma_{CG}$ represents a minimal uncertainty for the glucose sensor when accurate.

15. The method of claim 1, wherein the recursive filter is configured to estimate the glucose level of the person further based on at least one of:
- when the person eats a meal;
- when the person exercises; and
- when insulin is delivered to the person.

16. The method of claim 1 further comprising using the computing device to predict a future glucose level of the person with a regression analysis tool configured to predict the future glucose level based on the estimated glucose level of the person from the recursive filter.

17. The method of claim 16, wherein the regression analysis tool comprises a Gaussian process regression analysis.

18. The method of claim 17, wherein the Gaussian process regression analysis comprises a training algorithm configured to learn one or more characteristics of the person related to the glucose level of the person.

19. The method of claim 16 further comprising determining an uncertainty of the predicted future glucose level of the person.

20. The method of claim 16, wherein the regression analysis tool is configured to predict the future glucose level of the person further based on at least one of:
- when the person eats a meal;
- when the person exercises; and
- when insulin is delivered to the person.

21. A non-transitory computer-readable medium having a computer-executable instructions for performing a method for estimating a glucose level of a person having diabetes, the method comprising:
- receiving into a computer a plurality of measured glucose results from a glucose sensor coupled to the person;
- using the computer to analyze the plurality of measured glucose results with a probability analysis tool configured to determine a probability of glucose sensor accuracy PA based on the measured glucose results;
- using the computer to estimate the glucose level of the person with a recursive filter configured to estimate the glucose level based on the plurality of measured glucose results weighted with the probability of glucose sensor accuracy $P_A$; and
- using the computer to predict future glucose level of the person with a regression analysis tool configured to predict the future glucose level based on the estimated glucose level of the person from the recursive filter;
wherein the probability analysis tool comprises a hidden Markov model, wherein:
the hidden Markov model has two states:
a first state $S_A$ indicating the glucose sensor is accurate, and
a second state $S_I$ indicating the glucose sensor is inaccurate; and
the hidden Markov model is configured to determine the probability of glucose sensor accuracy $P_A$, based on a state of the hidden Markov model and the plurality of measured glucose results; and wherein probability of the hidden Markov model transitioning from the first state $S_A$ to second the state $S_I$ is $$PA \to I = \min\left[\left(1 - \frac{1}{1 + e^{-(\Delta CG + \alpha 1)/\alpha 2}}\right) + \left(1 - \frac{1}{1 + e^{-(CG + \alpha 3)/\alpha 4}}\right), 1\right]$$

where CG is a most-recent measured glucose result, $\Delta CG$ is a most-recent change in the plurality of measured glucose results, and $\alpha 1$, $\alpha 2$, $\alpha 3$ and $\alpha 4$ are constants related to characteristics of the glucose sensor.

22. The computer-readable medium of claim 21, wherein the computer comprises a blood glucose meter, an insulin pump, a microprocessor coupled to the glucose sensor, a cellular phone, a smart phone, a personal digital assistant, a personal computer, or a computer server.

23. The computer-readable medium of claim 21, wherein the glucose sensor comprises a continuous glucose monitoring system physically coupled to the person having diabetes and configured to automatically measure the glucose level of the person.

24. The computer-readable medium of claim 21, wherein the plurality of measured glucose results comprises periodic glucose measurements taken approximately every one minute.

25. The computer-readable medium of claim 21, wherein the probability analysis tool is configured to determine a probability of glucose sensor accuracy $P_A$ further based on at least one of:
when the person eats a meal;
when the person exercises;
when insulin is delivered to the person; and
one or more measurements from an impedance measuring device coupled to the person having diabetes and configured to measure impedance in the person.

26. The computer-readable medium of claim 21, wherein probability of the glucose sensor being in $S_I$ is based on a most-recent measured glucose result, a most-recent change in the plurality of measured glucose results, or a combination thereof.

27. The computer-readable medium of claim 21, wherein probability of remaining in the second state $S_I$ is $$P_{I \to I} = \max\left[\gamma P_{I_{k-1}} - \left(\frac{1}{1 + e^{-(\Delta CG + \alpha 5)/\alpha 6}}\right), 0\right],$$

where $\Delta CG$ is a most-recent change in the plurality of measured glucose results, $P_{I_{k-1}}$ is a previous probability of transitioning to or being in the second state $S_I$, and $\gamma$, $\alpha_5$, and $\alpha_6$ are constants related to characteristics of the glucose sensor.

28. The computer-readable medium of claim 21, wherein the probability of glucose sensor accuracy $P_A$ is $1 - [(P_{A \to I} \times S_A) + (P_{I \to I} \times S_I)]$, wherein $S_A=1$ when the hidden Markov model is in the first state $S_A$ and $S_A=0$ otherwise,
$S_I=1$ when the hidden Markov model is in the second state $S_I$ and $S_I=0$ otherwise,
$P_{A \to I}$ is a probability of transitioning from the first state $S_A$ to the second state $S_I$, and
$P_{I \to I}$ is a probability of remaining in the second state $S_I$ when in the second state $S_I$.

29. The computer-readable medium of claim 21, wherein the recursive filter is a Kalman filter or an Extended Kalman filter.

30. The computer-readable medium of claim 29, wherein the method further comprises using the computer to predict a future glucose level of the person with the Kalman filter or the Extended Kalman filter, wherein:
the Kalman filter or the Extended Kalman filter comprises a prediction step and a measurement step; and
the prediction step is performed one or more times in order to predict the future glucose level of the person.

31. The computer-readable medium of claim 29, wherein the Kalman filter or the Extended Kalman filter comprises a state vector, $x_k=[g\ \dot{g}\ \ddot{g}]^T$, where k represents a kth sample of the state vector, g represents the estimated glucose level of the person, $\dot{g}$ represents a first derivative of g, and $\ddot{g}$ represents a second derivative of g.

32. The computer-readable medium of claim 31, wherein using the computer to estimate the glucose level of the person comprises determining the state vector $$x_k = \hat{x}_k + K_k(z_k - H\hat{x}_k)P_A,$$

where $$\hat{x}_k = \begin{bmatrix} 1 & 1 & 0 \\ 0 & \beta_1 & 1 \\ 0 & 0 & \beta_2 \end{bmatrix} x_{k-1}, z_k = [CG\ \Delta CG]^T, H = \begin{bmatrix} 1 & 0 & 0 \\ 0 & 1 & 0 \end{bmatrix},$$

CG is a most-recent measured glucose result, $\Delta CG$ is a most-recent change in the plurality of measured glucose results, $K_k$ is a Kalman gain, $P_A$ is the probability of glucose sensor accuracy, and $\beta_1$ and $\beta_2$ are constants related to characteristics of the glucose sensor.

33. The computer-readable medium of claim 32, wherein the Kalman gain $K_k$ is based on a measurement uncertainty $R_k$ such that the measurement uncertainty $R_k$ is variable and is based on the probability of sensor accuracy.

34. The computer-readable medium of claim 33, wherein the measurement uncertainty $R_k$ is:

$$R_k = \min\left[\sum_{i=1}^{\tau} \frac{(C_{k-i} - \overline{C})^2}{\tau - 1} + P_I \sigma_{max}^2, \sigma_{max}^2\right] + \sigma_{CG}^2,$$

where $C_{k-i} = CG_{k-i} - Hx_{k-i}$, $\overline{C} = \frac{1}{\tau}\sum_{i=1}^{\tau} C_{k-i}$, $\tau$ represents a time history, $\sigma_{max}$ represents a maximum physiological variance for glucose in a person with poorly controlled diabetes, and $\sigma_{CG}$ represents a minimal uncertainty for the glucose sensor when accurate.

35. The computer-readable medium of claim 21, wherein the recursive filter is configured to estimate the glucose level of the person further based on at least one of:
when the person eats a meal;
when the person exercises; and
when insulin is delivered to the person.

36. The computer-readable medium of claim 21, wherein the regression analysis tool comprises a Gaussian process regression analysis.

37. The computer-readable medium of claim 36, wherein the Gaussian process regression analysis comprises a training algorithm configured to learn one or more characteristics of the person related to the glucose level of the person.

38. The computer-readable medium of claim 21, wherein the method further comprises determining an uncertainty of the predicted future glucose level of the person.

39. The computer-readable medium of claim 21, wherein the regression analysis tool is configured to predict the future glucose level of the person further based on at least one of:
when the person eats a meal;
when the person exercises; and
when insulin is delivered to the person.

40. An apparatus for estimating a glucose level of a person having diabetes, the apparatus comprising a microcontroller, an input device, and a display, wherein:
the microcontroller is electrically coupled to the input device configured to receive a plurality of measured glucose results from a glucose sensor coupled to the person, wherein the microcontroller is configured to receive the plurality of measured glucose results from the input device;
the microcontroller is configured to analyze the plurality of measured glucose results with a probability analysis tool configured to determine a probability of glucose sensor accuracy $P_A$ based on the plurality of measured glucose results;
the microcontroller is configured to estimate a glucose level of the person with a recursive filter configured to estimate the glucose level based on the plurality of measured glucose results weighted with the probability of glucose sensor accuracy $P_A$; and
the microcontroller is electrically coupled to the display such that the microcontroller is configured to transmit to the display information related to the estimate of the glucose level of the person; and
the microcontroller is further configured to predict a future glucose level of the person with a regression analysis tool configured to predict the future glucose level based on the estimated glucose level of the person from the recursive filter wherein the probability analysis tool comprises a hidden Markov model, wherein: the hidden Markov model has two states:
a first state $S_A$ indicating the glucose sensor is accurate, and
a second state $S_I$ indicating the glucose sensor is inaccurate; and
the hidden Markov model is configured to determine the probability of glucose sensor accuracy $P_A$, based on a state of the hidden Markov model and the plurality of measured glucose results; and wherein probability of the hidden Markov model transitioning from the first state $S_A$ to second the state $S_I$ is $$P_{A \to I} = \min\left[\left(1 - \frac{1}{1 + e^{-(\Delta CG + \alpha_1)/\alpha_2}}\right) + \left(1 - \frac{1}{1 + e^{-(CG + \alpha_3)/\alpha_4}}\right), 1\right]$$

where CG is a most-recent measured glucose result, $\Delta CG$ is a most-recent change in the plurality of measured glucose results, and $\alpha_1$, $\alpha_2$, $\alpha_3$ and $\alpha_4$ are constants related to characteristics of the glucose sensor.

41. The apparatus of claim 40, wherein the apparatus comprises a blood glucose meter, an insulin pump, a continuous glucose monitoring system, a cellular phone, a smart phone, a personal digital assistant, a personal computer, or a computer server.

42. The apparatus of claim 40, wherein the glucose sensor comprises a continuous glucose monitoring system physically coupled to the person having diabetes and configured to automatically measure a glucose level of the person.

43. The apparatus of claim 40, wherein the plurality of measured glucose results comprises periodic glucose measurements taken approximately every one minute.

44. The apparatus of claim 40, wherein the probability analysis tool is configured to determine a probability of glucose sensor accuracy $P_A$ further based on at least one of:
when the person eats a meal;
when the person exercises;
when insulin is delivered to the person; and
one or more measurements from an impedance measuring device coupled to the person having diabetes and configured to measure impedance in the person.

45. The apparatus of claim 40, wherein probability of the glucose sensor being in the second state $S_I$ is based on a most-recent measured glucose result, a most-recent change in the plurality of measured glucose results, or a combination thereof.

46. The apparatus of claim 40, wherein probability of the hidden Markov model remaining in the second state $S_I$ is $$P_{I \to I} = \max\left[\gamma P_{I_{k-1}} - \left(\frac{1}{1 + e^{-(\Delta CG + \alpha_5)/\alpha_6}}\right), 0\right],$$

where $\Delta CG$ is a most-recent change in the plurality of measured glucose results, $P_{I_{k-1}}$ is a previous probability of transitioning to or being in the second state $S_I$, and $\gamma$, $\alpha_5$, and $\alpha_6$ are constants related to characteristics of the glucose sensor.

47. The apparatus of claim 40, wherein probability of glucose sensor accuracy $P_A$ is $1 - [(P_{A \to I} \times S_A) + (P_{I \to I} \times S_I)]$, wherein $S_A$=1 when the hidden Markov model is in the first state $S_A$ and $S_A$=0 otherwise,
$S_I$=1 when the hidden Markov model is in the second state $S_I$ and $S_I$=0 otherwise,
$P_{A \to I}$ is a probability of transitioning from the first state $S_A$ to the second state $S_I$, and
$P_{I \to I}$ is a probability of remaining in the second state $S_I$ when in the second state $S_I$.

48. The apparatus of claim 40, wherein the recursive filter is a Kalman filter or an Extended Kalman filter.

49. The apparatus of claim 48, wherein the microcontroller is further configured to predict a future glucose level of the person with the Kalman filter or the Extended Kalman filter, wherein:
the Kalman filter or the Extended Kalman filter comprises a prediction step and a measurement step; and
the prediction step is performed one or more times in order to predict the future glucose level of the person.

50. The apparatus of claim 48, wherein the Kalman filter or the Extended Kalman filter comprises a state vector, $x_k = [g \; \dot{g} \; \ddot{g}]^T$, where k represents a kth sample of the state vector, g represents the estimated glucose level of the person, $\dot{g}$ represents a first derivative of g, and $\ddot{g}$ represents a second derivative of g.

51. The apparatus of claim 50, wherein the microcontroller is configured to estimate the glucose level of the person by determining the state vector $$x_k = \hat{x}_k + K_k(z_k - H\hat{x}_k)P_A,$$

where $$\hat{x}_k = \begin{bmatrix} 1 & 1 & 0 \\ 0 & \beta_1 & 1 \\ 0 & 0 & \beta_2 \end{bmatrix} x_{k-1}, z_k = [\, CG \quad \Delta CG \,]^T, H = \begin{bmatrix} 1 & 0 & 0 \\ 0 & 1 & 0 \end{bmatrix},$$

CG is a most-recent measured glucose result, $\Delta$CG is a most-recent change in the plurality of measured glucose results, $K_k$ is a Kalman gain, $P_A$ is the probability of glucose sensor accuracy, and $\beta_1$ and $\beta_2$ are constants related to characteristics of the glucose sensor.

52. The apparatus of claim 51, wherein the Kalman gain $K_k$ is based on a measurement uncertainty $R_k$ such that the measurement uncertainty $R_k$ is variable and is based on the probability of sensor accuracy.

53. The apparatus of claim 52, wherein the measurement uncertainty $R_k$ is:

$$R_k = \min\left[\sum_{i=1}^{\tau} \frac{(C_{k-i} - \overline{C})^2}{\tau - 1} + P_l \sigma_{max}^2, \sigma_{max}^2\right] + \sigma_{CG}^2,$$

where $C_{k-i} = CG_{k-i} - Hx_{k-i}$, $\overline{C} = \frac{1}{\tau}\sum_{i=1}^{\tau} C_{k-i}$, represents a time history, $\sigma_{max}$ represents a maximum physiological variance for glucose in a person with poorly controlled diabetes, and $\sigma_{CG}$ represents a minimal uncertainty for the glucose sensor when accurate.

54. The apparatus of claim 40, wherein the recursive filter is configured to estimate the glucose level of the person further based on at least one of:
when the person eats a meal;
when the person exercises; and
when insulin is delivered to the person.

55. The apparatus of claim 40, wherein the regression analysis tool comprises a Gaussian process regression analysis.

56. The apparatus of claim 55, wherein the Gaussian process regression analysis comprises a training algorithm configured to learn one or more characteristics of the person related to the glucose level of the person.

57. The apparatus of claim 40, wherein the regression analysis tool is configured to determine an uncertainty of the predicted future glucose level of the person.

58. The apparatus of claim 40, wherein the regression analysis tool is configured to predict the future glucose level of the person further based on at least one of:
when the person eats a meal;
when the person exercises; and
when insulin is delivered to the person.

* * * * *